United States Patent [19]

Bahal et al.

[11] Patent Number: 5,192,784
[45] Date of Patent: Mar. 9, 1993

[54] ETANIDAZOLE INJECTABLE SOLUTION

[75] Inventors: Surendra M. Bahal, Wayne, Pa.; Kenneth S. Field, New Castle; Michael B. Maurin, Newark, both of Del.

[73] Assignee: Du Pont Merck Pharmaceutical Company, Wilmington, Del.

[21] Appl. No.: 906,022

[22] Filed: Jun. 26, 1992

Related U.S. Application Data

[63] Continuation of Ser. No. 709,174, Jun. 3, 1991, abandoned.

[51] Int. Cl.$^5$ ............................................. A61K 31/415
[52] U.S. Cl. .................................................... 514/398
[58] Field of Search ......................................... 514/398

[56] References Cited

U.S. PATENT DOCUMENTS 3,679,698  7/1972  Beaman et al.
4,371,540  2/1983  Lee et al. ............................ 514/398

OTHER PUBLICATIONS

The Pharmacopeia of the United States of America, 18th edition, 1970, p. 593.
Remingtons Pharmaceutical Sciences, 15th edition, Mack, Easton, Pa., 1975, pp. 268-270, 283-284, 1405-1412, 1365-1367).

Primary Examiner—Alan Siegel
Assistant Examiner—Rebecca Cook
Attorney, Agent, or Firm—Blair Q. Ferguson; Gildo E. Fato; Margaret A. Horn

[57] ABSTRACT

Physically and chemically stable pharmaceutical compositions useful for administering etanidazole by injection are described. These compositions are essentially aqueous solutions having a pH less than or equal to 5.5, and containing etanidazole, a buffer system, and a tonicity-adjusting agent, and they are optionally stabilized by the addition of a stabilizing agent or by autoclaving.

7 Claims, 1 Drawing Sheet

ETANIDAZOLE INJECTABLE SOLUTION

This application is a continuation of application Ser. No. 07/709,174 filed Jun. 3, 1991, now abandoned.

BACKGROUND OF THE INVENTION

The present invention relates to a pharmaceutical composition for administering etanidazole by injection. More particularly, this invention provides solution formulations containing higher concentrations of etanidazole, and having better physical and chemical stability than other known formulations of etanidazole.

Formulations of pharmaceutical compositions and processes for preparing them depend upon the properties of the active ingredient, the desired route of administration and the end use to be obtained. Etanidazole is a substituted nitroimidazole that sensitizes tumor cells to radiation therapy. The compound and methods for its synthesis are described in U.S. Pat. No. 3,679,698. Its use as a radiosensitizing agent is described in U.S. Pat. No. 4,371,540. The preferred route of administration of radiosensitizers is by intravenous injection or infusion. The intravenous route of administration affords rapid delivery of the drug to the target tissue, complete bioavailability, and is more predictable and controllable than other routes. Solution formulations for intravenous administration must be essentially free of particulate matter, and they must be sterile. They must be physically and chemically stable, so that efficacy and safety are predictable. Another property generally needed for cancer chemotherapeutic agents, such as etanidazole, is a high concentration of the active ingredient. This is desirable because therapy is often guided toward the maximum tolerated dose. Etanidazole formulations are subject to all of these requirements.

Formulations for intravenous administration can be prepared as solutions that are ready to inject or ready to dilute with an infusion solution, or they can be prepared as dry powders that must be dissolved before use. Solution formulations are preferred over dry powders, when feasible, because of ease of use, ease of manufacture, and reduced cost.

SUMMARY OF THE INVENTION

Figure 1:
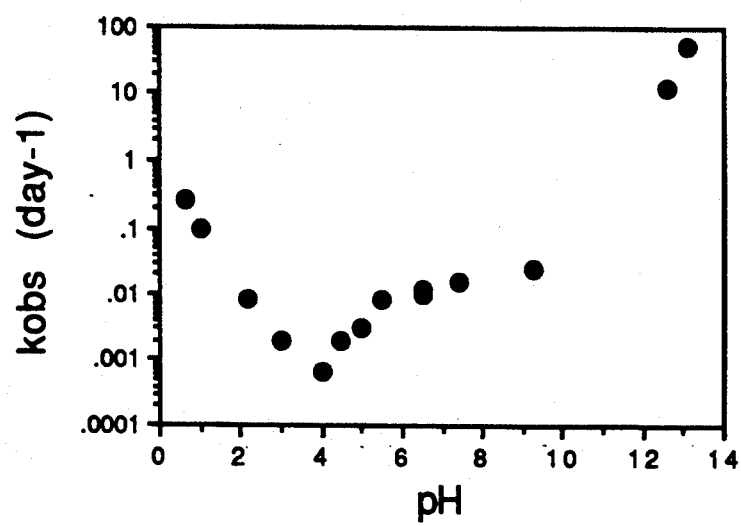
FIG. 1 is a pH Profile for the Hydrolysis of Etanidazole at 80° C.

According to the present invention it has been discovered that pharmaceutical compositions of the drug etanidazole can be prepared that have improved physical and chemical stability, a high concentration of the active drug, and are ready-to-use solutions. These pharmaceutical compositions are useful for intravenous injection or infusion to treat cancer. More particularly, the compositions contain an effective amount of etanidazole, a suitable buffer system selected to give a pH of the final composition of less than 5.5, a tonicity-adjusting agent, and optionally a stabilizing agent, said composition being optionally autoclaved. Advantages of such a composition include, but are not limited to: ease of use, ease of manufacture, reduced cost, increased shelf-life, and a reduced incidence of particulate formation in the product.

DETAILED DESCRIPTION OF THE INVENTION

Ready-to-use injectable solution formulations of etanidazole with improved chemical and physical stability are preferably composed of an effective amount of etanidazole, a suitable buffer system to yield a final solution pH <5.5, one or more tonicity adjusting agents, and optionally a stabilizing agent selected from the group consisting of imidazole, ethanolamine, diethanolamine, triethylamine, triethanolamine, or ethylenediamine. Said compositions are optionally autoclaved for sterilization.

Specifically preferred compositions use a buffer system of citrate, acetate, or phosphate, wherein the pH is 3.5–4.0. The specifically preferred tonicity adjusting agent is sodium chloride. These compositions are preferably terminally sterilized by autoclaving. A typical autoclaving process is to expose the containers of the composition to steam under pressure for at least 15 minutes at a minimum temperature of 121° C.

The preferred concentration of etanidazole in the composition is 20–150 mg/ml. Specifically preferred concentrations are 50–100 mg/ml. Preferred concentrations of the stabilizing agents are 0.001% to 5%. Specifically preferred concentrations are 0.05 to 1%.

The k values shown in Tables 1–5 and FIG. 1 should be multipled by a factor of 2.303 to provide the actual k value.

EXAMPLE 1

The chemical stability of etanidazole was evaluated in solutions of varying composition stored at 80° C. Etanidazole was placed into suitable containers and sufficient buffer was added to result in a 1 mg/ml solution. A constant ionic strength of 0.3 was maintained with potassium chloride. All solutions were prepared in triplicate. The solution was divided into 2 ml sealed glass vials and was placed into cardboard storage boxes to protect the compound from light. At appropriate intervals, samples were removed from the stability chamber and cooled to room temperature. An aliquot of the sample was diluted with mobile phase containing internal standard prior to HPLC analysis. For those pH conditions where degradation was rapid, the sample aliquot was immediately quenched to neutral pH and room temperature.

Data were analyzed using methods as described by Martin et al. in "Physical Pharmacy", 3rd ed, pp 352–395 (1983). The degradation of etanidazole followed apparent first-order kinetics. The degradation rate constants ($k_{obs}$) were calculated by least squares regression, and are summarized in Table 1.

TABLE 1

Observed First-Order Rate Constants for the Solution Stability of Etanidazole at 80° C.

| Buffer | $k_{obs}$ (day$^{-1}$)* |
|---|---|
| 0.3M HCl pH 0.62 | $0.263 \pm 3.84 \times 10^{-3}$ |
| 0.1M HCl pH 1.0 | $9.61 \times 10^{-2} \pm 3.36 \times 10^{-3}$ |
| 0.01M HCl pH 2.2 | $8.24 \times 10^{-3} \pm 1.16 \times 10^{-3}$ |
| 0.05M Citrate pH 3.0 | $5.75 \times 10^{-3} \pm 5.20 \times 10^{-5}$ |
| 0.1M Citrate pH 3.0 | $8.82 \times 10^{-3} \pm 6.12 \times 10^{-4}$ |
| 0.25M Citrate pH 3.0 | $1.97 \times 10^{-2} \pm 1.15 \times 10^{-3}$ |
| 0.05M Acetate pH 4.0 | $1.19 \times 10^{-3} \pm 1.00 \times 10^{-5}$ |
| 0.1M Acetate pH 4.0 | $1.85 \times 10^{-3} \pm 5.20 \times 10^{-5}$ |
| 0.25M Acetate pH 4.0 | $3.42 \times 10^{-3} \pm 1.81 \times 10^{-4}$ |
| 0.05M Citrate pH 4.5 | $3.36 \times 10^{-3} \pm 1.23 \times 10^{-4}$ |
| 0.1M Citrate pH 4.5 | $5.87 \times 10^{-3} \pm 4.06 \times 10^{-4}$ |
| 0.18M Citrate pH 4.5 | $7.89 \times 10^{-3} \pm 6.11 \times 10^{-4}$ |

TABLE 1-continued

Observed First-Order Rate Constants for the
Solution Stability of Etanidazole at 80° C.

| Buffer | $k_{obs}$ (day$^{-1}$)* |
|---|---|
| 0.05M Acetate pH 5.0 | $3.86 \times 10^{-3} \pm 2.69 \times 10^{-5}$ |
| 0.1M Acetate pH 5.0 | $5.16 \times 10^{-3} \pm 1.04 \times 10^{-4}$ |
| 0.25M Acetate pH 5.0 | $8.01 \times 10^{-3} \pm 1.10 \times 10^{-4}$ |
| 0.02M Citrate pH 5.5 | $8.43 \times 10^{-3} \pm 3.51 \times 10^{-5}$ |
| 0.05M Citrate pH 5.5 | $9.57 \times 10^{-3} \pm 7.37 \times 10^{-5}$ |
| 0.1M Citrate pH 5.5 | $1.01 \times 10^{-2} \pm 2.08 \times 10^{-4}$ |
| 0.013M Citrate pH 6.5 | $1.06 \times 10^{-2} \pm 1.53 \times 10^{-4}$ |
| 0.03M Citrate pH 6.5 | $1.19 \times 10^{-2} \pm 2.08 \times 10^{-4}$ |
| 0.065M Citrate pH 6.5 | $1.32 \times 10^{-2} \pm 0$ |
| 0.05M Phosphate pH 6.5 | $1.35 \times 10^{-2} \pm 5.77 \times 10^{-5}$ |
| 0.1M Phosphate pH 6.5 | $1.49 \times 10^{-2} \pm 1.00 \times 10^{-4}$ |
| 0.025M Phosphate pH 6.5 | $1.95 \times 10^{-2} \pm 8.00 \times 10^{-5}$ |
| 0.05M Phosphate pH 7.4 | $1.68 \times 10^{-2} \pm 4.07 \times 10^{-4}$ |
| 0.1M Phosphate pH 7.4 | $1.87 \times 10^{-2} \pm 2.00 \times 10^{-4}$ |
| 0.135M Phosphate pH 7.4 | $1.83 \times 10^{-2} \pm 3.50 \times 10^{-4}$ |
| 0.05M Borate pH 9.2 | $3.33 \times 10^{-2} \pm 1.91 \times 10^{-3}$ |
| 0.1M Borate pH 9.2 | $3.82 \times 10^{-2} \pm 1.08 \times 10^{-3}$ |
| 0.25M Borate pH 9.2 | $5.96 \times 10^{-2} \pm 5.83 \times 10^{-4}$ |
| 0.1M NaOH pH 12.6 | $13.1 \pm 0.399$ |
| 0.3M NaOH pH 13.1 | $52.9 \pm 3.23$ |

*Mean ± standard deviation (n = 3)

In the intermediate pH range where buffers were employed, the observed first-order rate constant can be defined at any given pH with the following equation;

$$k_{obs} = k_{H+}[H+] + k_o + k_{OH-}[OH-] + k_B[B_T]$$

where $k_{H+}$ and $k_{OH-}$ are the second-order specific acid and specifiic base catalysis rate constants, respectively $k_B$ is the second-order rate constant for the catalysis due to the buffer, and $[B_T]$ is the total buffer concentration. Plotting $k_{obs}$ vs $[B_T]$ yields a slope of $k_B$ and a y-intercept of $k_{H+}[H+] + k_o + k_{OH-}[OH-]$, the observed rate constant extrapolated to zero buffer concentration (k'). The second order rate constants are provided in Table 2. The observed rate constant extrapolated to zero buffer concentration (k') are used to generate the pH-rate profile (FIG. 1).

The buffer systems permit pH control through the equilibrium of their acidic and basic forms. Utilizing these equilibria, the rate constants for the individual buffer species may be calculated. In the acetate buffers, the second-order rate constant for the catalysis due to the acetate buffer is defined as follows;

where $f_{CH_3COOH}$ is the fraction of the acetate buffer in the neutral form, $k_{(CH_3COOH)}$ is the second-order rate constant for the catalysis due to the acetic acid species, $f_{CH_3COO-}$ is the fraction of the acetate buffer in the ionized form and $k_{CH_3COO-}$ is the second-order rate constant for the catalysis due to the acetate anion. Employing the same buffer for various pH conditions permits the determination of the second-order rate constants for the various species (Table 3).

The effect of initial etanidazole concentration on the rate of decomposition was examined in 0.05M citrate pH 5.5, at 80° C. Initial concentrations of 1, 25 and 50 mg/ml were employed. The results indicate that the degradation of etanidazole is not concentration dependent in this range (Table 4).

TABLE 2

The Second-Order Rate Constants for the Buffer Catalysis and the First-Order Rate Constant Extrapolated to Zero Buffer Concentration for the Solution Stability of Etanidazole at 80° C.

| Buffer | k' (day$^{-1}$) | $k_B$ (day$^{-1}$M$^{-1}$) |
|---|---|---|
| Citrate pH 3.0 | $2.04 \times 10^{-3}$ | $7.04 \times 10^{-2}$ |
| Acetate pH 4.0 | $6.88 \times 10^{-4}$ | $1.10 \times 10^{-2}$ |
| Citrate pH 4.5 | $1.97 \times 10^{-3}$ | $3.40 \times 10^{-2}$ |
| Acetate pH 5.0 | $2.96 \times 10^{-3}$ | $2.03 \times 10^{-2}$ |
| Citrate pH 5.5 | $8.24 \times 10^{-3}$ | $1.98 \times 10^{-2}$ |
| Citrate pH 6.5 | $1.02 \times 10^{-2}$ | $4.81 \times 10^{-2}$ |
| Phosphate pH 6.5 | $1.19 \times 10^{-2}$ | $3.02 \times 10^{-2}$ |
| Phosphate pH 7.4 | $1.61 \times 10^{-2}$ | $1.90 \times 10^{-2}$ |
| Borate pH 9.2 | $2.58 \times 10^{-2}$ | $1.34 \times 10^{-1}$ |

TABLE 3

The Second-Order Rate Constants for the Various Buffer Species for the Solution Stability of Etanidazole at 80° C.

| Buffer Species | $k_B$ (day$^{-1}$M$^{-1}$) |
|---|---|
| Citric Acid | $8.89 \times 10^{-2}$ |
| Dihydrogen citrate$^{-1}$ | $4.58 \times 10^{-2}$ |
| Hydrogen citrate$^{-2}$ | $7.11 \times 10^{-3}$ |
| Citrate$^{-3}$ | $8.12 \times 10^{-2}$ |
| Acetic acid | $8.13 \times 10^{-3}$ |
| Acetic$^{-1}$ | $2.74 \times 10^{-2}$ |
| Dihydrogen phosphate$^{-1}$ | $3.41 \times 10^{-2}$ |
| Hydrogen phosphate$^{-2}$ | $1.01 \times 10^{-2}$ |

TABLE 4

Effect of Etanidazole Initial Concentration on the observed First-Order Rate Constants for the Degradation of Etanidazole in 0.05M Citrate, pH 5.5, at 80° C.

| Ionic Concentration (mg/ml) | $k_{obs}$ (day$^{-1}$) |
|---|---|
| 1 | $9.57 \times 10^{-3} \pm 7.37 \times 10^{-5}$ |
| 25 | $1.27 \times 10^{-2} \pm 5.86 \times 10^{-4}$ |
| 50 | $1.27 \times 10^{-2} \pm 1.53 \times 10^{-4}$ |

The impact of the ionic strength of the buffer system on the rate of decomposition was examined in 0.1M acetate, pH 5.0, at 80° C. Ionic strengths of 0.15, 0.30 and 0.60 were employed. The results indicate that the increasing the ionic strength results in a negligible effect on the degradation rate of etanidazole (Table 5).

In summary, the hydrolysis of etanidazole followed apparent first-order kinetics over the pH range of 0.6 to 12.6, at 80° C. Citrate and acetate were both catalytic at the pH minimum, with citrate being a stronger catalyst than acetate. Concentration and ionic strength had negligible effects on the stability. Analysis of the degradation product indicated that the primary route of degradation is through the hydrolysis of the amide linkage. The overall rate constant was minimum at a pH of approximately 4.

FIG. 1. pH-rate profile for the hydrolysis of etanidazole at 80° C. All rate values have been extropolated to zero buffer concentration.

TABLE 5

Effect of Ionic Strength on the Observed First-Order Rate Constant for the Degradation of Etanidazole in 0.1M Acetate, pH 5.0, at 80° C.

| Ionic Strength | $k_{obs}$ (day$^{-1}$) |
|---|---|
| 0.15 | $5.90 \times 10^{-3} \pm 1.08 \times 10^{-4}$ |
| 0.30 | $5.16 \times 10^{-3} \pm 1.04 \times 10^{-4}$ |
| 0.60 | $5.18 \times 10^{-3} \pm 3.06 \times 10^{-4}$ |

EXAMPLE 2

Solubility studies were carried out by placing excess etanidazole into a suitable container and rotating end-to-end for twenty four hours at 25° C. The suspension was passed through a 0.2µ filter with the first portion discarded to ensure saturation of the filter. An aliquot of the filtrate was diluted and analyzed by HPLC and the remainder of the filtrate was employed for pH determination.

Etanidazole was soluble in water at 68.1 mg/ml, pH 6.5. Changes in pH have a negligible effect on the solubility. The solubility was between 59.2 and 71.7 mg/ml over a pH range of 0.72 to 13.2 with no discernible trends in the data. Initially the etanidazole dissolved at concentrations in excess of 150 mg/ml. However, after rotating for 24 hours crystals appeared.

The crystals were isolated and characterized. The material appeared needle-shaped. The retention time of the precipitate was in agreement with that of etanidazole. The precipitate contained 5.6% water as determined by Karl Fischer analysis. Thermal analysis of the precipitate revealed two endothermic peaks at 64.1° C. and 142.2° C. Another sample was heated to 100° C. in a vented pan that permitted volatile evolution. The sample pan was cooled to room temperature and reheated to 200° C. The resulting thermogram was comparable to that of the original drug substance, with an endothermic peak at 165.6° C. The additional peak on thermal analysis of the precipitate can be attributed to water of hydration, with the stoichiometry suggesting a monohydrate.

Thus, the solubility studies were actually determining the solubility of the more stable monohydrate form of etanizdazole. The solubility increased as function of temperature to 149 mg/ml and 358 mg/ml at 37° C. and 50° C., respectively.

EXAMPLE 3

Experimental aqueous buffer solution formulations containing 50 mg/ml etanidazole were observed to occasionally develop crystalline particulates when stored at 4° C. Sixteen samples of etanidazole solutions at various pHs, which contained crystals, were heated in a 56° C. water bath for 1 hour to dissolve the crystals. After heating, the samples were divided evenly. Half of the samples were left as non-autoclaved samples and the other half were autoclaved for 15 minutes at 121° C. After 4 days of storage at 4° C., 3 of 8 non-autoclaved samples contained crystals again. Results are summarized as follows.

| Batch # | pH | Autoclaved # Vials | Non-Autoclaved # Vials |
|---|---|---|---|
| A | 4.0 | 1 | 1 |
| B | 5.0 | 1 | 1 |
| C | 5.5 | 2 | 3 *(2) |
| D | 4.0 | 1 | 1 *(1) |
| E | 3.5 | 1 | |
| F | 3.0 | 2 | 2 |

*(# vials with subsequent crystal formation)

Further studies were done in which etanidazole (50 mg/ml) solutions at pH 3.0, 3.5, and 4.0 were prepared and the effect of autoclaving was evaluated. At pH 3.0, 0 of 48 autoclaved samples and 0 of 48 non-autoclaved samples developed crystals when stored at 4° C. over 43 days. At pH 3.5, 0 of 49 autoclaved samples developed crystals, and 3 of 50 non-autoclaved samples developed crystals when stored at 4° C. over 43 days. At pH 4.0, 0 of 50 autoclaved samples developed crystals when stored at 4° C. for 43 days, but 1 of 50 non-autoclaved samples developed crystals. These studies clearly show that autoclaving prevents the formation of crystals when the etanidazole solutions are subsequently stored at 4° C.

EXAMPLE 4

The effects of additives on the apparent solubility of etanidazole were evaluated. As described in Example 2, without additives etanidazole was initially soluble at concentrations greater than 150 mg/ml, but eventually a precipitate formed which was apparently etanidazole hydrate, and which had a solubility between 59.2 and 71.7 mg/ml. Possible effects of additives are to inhibit the crystallization of etanidazole hydrate and to solubilize etanidazole hydrate.

Solutions were prepared containing 50, 100 and 150 mg/ml etanidazole and concentrations in excess of etanidazole solubility, with 1% imidazole, 1% ethanolamine, or 0.1% diethanolamine as additives. Solutions were mixed by rotating end-to-end for 72 hours at room temperature. For sample containing 1% imidazole and excess etanidazole, the excess solid appeared to have been converted to etanidazole hydrate. Solutions containing 1% imidazole and up to 150 mg/ml etanidazole remained clear and free of particulates. These were placed in 4° C. storage. Within 2 hours the 150 mg/ml solution showed crystal formation, but the 50 and 100 mg/ml solutions remained clear for up to 1 month at 4° C. In the case of solutions containing 1% ethanolamine or 0.1% diethanolamine as additives and excess or 150 mg/ml etanidazole, crystalline material had found within 24 hours at room temperature, but the 50 mg/ml and 100 mg/ml solutions remained clear at room temperature for 72 hours. These samples were placed at 4° C. Within 24 hours, solutions containing 100 mg/ml etanidazole and 1% ethanolamine showed crystallization, whereas those containing 50 mg/ml etanidazole remained clear for at least 1 month. Within 24 hours at 4° C., 1 of 3 vials containing solutions of 100 mg/ml etanidazole and 0.1% diethanolamine showed crystallization. After 2 months at 4° C., 1 of the 3 vials remained free of crystals. The 50 mg/ml etanidazole solution with 0.1% diethanolamine remained clear for at least 2 months at 4° C. These results indicate that these additives stabilize etanidazole solutions, inhibiting crystal formation at room temperature or when stored at 4° C.

Equilibrium solubility of etanidazole in 0.05M acetate or citrate buffers at pH 4.0 and the effects of additives were determined. Results are summarized as follows.

| Buffer | Additive | Solubility at 4° C. mg/ml, mean ± SD) |
|---|---|---|
| Acetate | None | 83.4 ± 26.3 |
| Acetate | 0.13% Ethylenediamine | 54.8 ± 30.9 |
| Acetate | 0.065% Imidazole | 64.8 ± 32.1 |
| Citrate | None | 36.6 ± 6.4 |
| Citrate | 0.13% Ethylenediamine | 61.5 ± 33.9 |
| Citrate | 0.065% Imidazole | 95.4 ± 3.7 |

Solutions containing acetate buffer, or ethylenediame as an additive, had greatest variability in etanidazole solubility. Imidazole increased etanidazole solubility in citrate buffer.

EXAMPLE 5

A ready-made solution formulation of etanidazole is made comprising the following:

|  | For 1 ml |
| --- | --- |
| Etanidazole | 50 mg |
| Citric Acid | 2.03 mg |
| Sodium Citrate | 1.76 mg |
| Sodium Chloride | 2.12 mg |
| Hydrochloric Acid | To adjust pH |
| Sodium Hydroxide | To adjust pH |
| Water for Injection | qs ad 1 ml |
| Reasonable variations that may be employed: | |
|  | Range |
| Citric Acid | 1–10 mg/ml |
| Sodium Citrate | 1–10 mg/ml |
| Sodium Chloride | 0–9 mg/ml |

Required volume of the bulk solution is packaged in appropriate vials to obtain 0.5, 1 and 2 g products. Products are autoclaved at 121° C. for 15 minutes.

What is claimed:

1. A stable, injectable, ready to use aqueous pharmaceutical composition having a pH in the range of 3.0 to 4.5, and comprising:
   a) a chemotherapeutically effective amount of etanidazole in an amount of from about 20 to 150 mg of etanidazole/ml of composition;
   b) a buffer system selected from the group consisting of citrate, acetate and phosphate,
   c) a tonicity adjusting agent which is sodium chloride; and
   d) a stabilizing agent selected from the group consisting of imidazole, ethanolamine, diethanolamine, triethanolamine, thiethylamine and ethylenediamine in an amount of about 0.001% to about 5% of the composition and effective to inhibit precipitation of the etanidazole;
   e) said composition minimizing the degration of etanidazole by hydrolysis, whereby the stability of etanidazole in an aqueous composition is enhanced.

2. A composition of claim 1 wherein the pH is between about 3.5–4.0

3. A composition of claim 2 wherein the pH is about 3.8.

4. A composition of claim 1 wherein the composition is autoclaved.

5. A pharmaceutical composition of claim 1 wherein component a) is present in an amount of about 50–100 mg/mL, component, b) is present in amount to yield a pH of about 4 and a stabilizing agent is present in a concentration of about 0.05% to 1%.

6. A pharmaceutical composition of claim 1 wherein the buffer system is citrate.

7. A pharmaceutical composition of claim 5 wherein the buffer system is citrate.

* * * * *